(12) United States Patent
Spedini

(10) Patent No.: US 12,352,736 B2
(45) Date of Patent: Jul. 8, 2025

(54) PNEUMATIC MEMBRANE GASOMETER FOR THE STORAGE OF HYDROGEN GAS AT LOW PRESSURE

(71) Applicant: ECOMEMBRANE SPA, Gadesco-Pieve Delmona (IT)

(72) Inventor: Lorenzo Spedini, Cremona (IT)

(73) Assignee: ECOMEMBRANE SPA, Gadesco-Pieve Delmona (IT)

( * ) Notice: Subject to any disclaimer, the term of this patent is extended or adjusted under 35 U.S.C. 154(b) by 124 days.

(21) Appl. No.: 18/551,521

(22) PCT Filed: Mar. 21, 2022

(86) PCT No.: PCT/IT2022/050059
§ 371 (c)(1),
(2) Date: Sep. 20, 2023

(87) PCT Pub. No.: WO2022/201208
PCT Pub. Date: Sep. 29, 2022

(65) Prior Publication Data
US 2024/0167638 A1    May 23, 2024

(30) Foreign Application Priority Data
Mar. 22, 2021  (IT) .................. 102021000006764

(51) Int. Cl.
*G01N 33/00*       (2006.01)
*F17C 3/00*        (2006.01)

(52) U.S. Cl.
CPC .......... *G01N 33/0027* (2013.01); *F17C 3/00* (2013.01); *F17C 2201/0185* (2013.01);
(Continued)

(58) Field of Classification Search
CPC .................. G01N 33/0027; F17C 3/00; F17C 2201/0185; F17C 2203/0631;
(Continued)

(56) References Cited

U.S. PATENT DOCUMENTS

H80 H     7/1986  Lewis et al.

FOREIGN PATENT DOCUMENTS

| AT | 388158 B | 5/1989 | |
| EP | 1338843 B1 * | 7/2010 | ............ C12M 21/04 |

(Continued)

OTHER PUBLICATIONS

KR 101223985 B1-English Translation (Year: 2013).*
International Search Report and Written Opinion of the ISA for PCT/IT2022/050059 mailed May 25, 2022, 12 pages.

*Primary Examiner* — Craig M Schneider
*Assistant Examiner* — Christopher M Afful
(74) *Attorney, Agent, or Firm* — NIXON & VANDERHYE

(57) ABSTRACT

Disclosed is a pneumatic membrane gasometer for the storage of hydrogen gas at low pressure. The gasometer includes: a first bag-shaped membrane delimiting a hydrogen storage chamber; a second membrane partially delimiting a pressurization chamber superimposed, at least in part, on the storage chamber; a third membrane, placed resting on top of the first membrane, fixed in an impermeable manner at least to the second membrane, defining, with the first membrane, a cavity open towards the outside of the gasometer; hydrogen supply and discharge unit associated with the storage chamber; pressurization unit; mechanical anchor to a base surface of the first, second and third membranes; and a natural passive ventilation system to vent any hydrogen (Continued)

losses to the outside, including a duct adapted to connect cavity to the outside environment passing through the pressurization chamber.

15 Claims, 2 Drawing Sheets

(52) U.S. Cl.
CPC ............... *F17C 2203/0631* (2013.01); *F17C 2203/0685* (2013.01); *F17C 2205/0364* (2013.01); *F17C 2221/012* (2013.01); *F17C 2223/033* (2013.01); *F17C 2250/0452* (2013.01); *F17C 2250/0491* (2013.01); *F17C 2260/036* (2013.01); *F17C 2260/038* (2013.01); *F17C 2270/0134* (2013.01)

(58) Field of Classification Search
CPC ...... F17C 2203/0685; F17C 2205/0364; F17C 2221/012; F17C 2223/033; F17C 2250/0452; F17C 2250/0491; F17C 2260/036; F17C 2260/038; F17C 2270/0134; F17C 2201/018; F17B 1/26; F17B 1/12; B67D 7/0244
USPC .......................................................... 141/346
See application file for complete search history.

(56) References Cited

FOREIGN PATENT DOCUMENTS

| EP | 2746385 | A2 | | 6/2014 | |
|----|---------|-----|---|--------|---|
| EP | 3276245 | A1 | * | 1/2018 | ............. F17C 3/022 |
| GB | 2487564 | A | | 8/2012 | |
| KR | 101223985 | B1 | * | 1/2013 | ............. B65D 88/04 |

\* cited by examiner

PNEUMATIC MEMBRANE GASOMETER FOR THE STORAGE OF HYDROGEN GAS AT LOW PRESSURE

CROSS-REFERENCE TO RELATED APPLICATIONS

This application is the U.S. national phase of International Application No. PCT/IT2022/050059 filed Mar. 21, 2022 which designated the U.S. and claims priority to IT 102021000006764 filed Mar. 22, 2021, the entire contents of each of which are hereby incorporated by reference.

TECHNICAL FIELD

The present invention relates to the industrial field of gas storage systems, and more particularly it concerns a pneumatic membrane gasometer for the storage of hydrogen gas at low pressure.

BACKGROUND ART

Pneumatic membrane gasometers, also called membrane gas holders or pressure gasholders, generally comprise a first membrane, which delimits a gas storage chamber above a gas-impermeable base surface, and a second membrane, adapted to create a (generally air) pressurization chamber, adjacent to said gas storage chamber.

Said base surface may, for example, be a surface of a liquid, or another membrane joined to the first membrane along the edge.

The second membrane, in addition to partially delimiting the pressurized air chamber, also performs the function of protecting the innermost membrane from weather, atmospheric agents and impacts against external bodies.

The storage chamber is connected to supply and discharge pipes for the gas contained therein. Instead, the pressurization chamber is connected to an auxiliary air fan, which allows a certain pressure to be maintained therein. In this way, the thrust exerted by the pressurization chamber on the gas storage chamber enables the gas to be supplied at the desired pressure, depending on the use of said gas.

The two chambers are anchored to the ground along the edge of the gasometer and comprise air and gas discharge valves to control the operating pressures.

The membranes are generally made of flexible material, such as polyester fibre fabric, covered or coated with a layer of plastic material, such as PVC.

In order to ensure the operation and safety of membrane gasometers, the impermeability of the chambers is above all essential. In fact, there must be no passage of gas from the storage chamber to the air pressurization chamber and vice versa, and no losses of gas or air to the outside.

The impermeability between the chambers is in fact entrusted to the integrity of the first membrane and the sealed closure of its lower edge on the base surface of the gasometer.

In the event of cracks, even of very small size, in the first membrane, particularly at the joints between the various elements of which it is formed or at the flanged connections, or of imperfect sealing of the lower edge of said membrane, or even merely of the porosity of the material, gas can pass from the storage chamber to the air pressurization chamber. This always takes place from the gas chamber to the air chamber, as the pressure of the gas is equal to the pressurization of the air plus the pressure increase caused by the weight of the first membrane. It should be borne in mind that the slightest leakage of gas into the air chamber is sufficient to cause an explosive mixture to form inside said chamber, resulting in very serious safety risks.

The importance of the seal and impermeability of the chambers is even greater in the case of gasometers adapted to store hydrogen in gaseous state.

Due to the small molecular size of hydrogen, it passes much more easily than other combustible gases, such as methane, through the membranes, which still have a minimal porosity.

The hydrogen molecule has a very low explosion ignition point: a small spark generated by friction or a build-up of electrostatic charges on a surface is sufficient to cause an explosion.

The hydrogen molecule is moreover characterized by a wide explosion range in air mixture: hydrogen detonates starting from concentrations in air of 4% by volume, and continues to be in a potentially explosive atmosphere up to a concentration in air of 75.6% by volume.

The conventional membrane gasometers described above have certain limitations and disadvantages in their particular application with hydrogen.

Said first PVC-coated polyester fibre membrane that delimits the gas storage chamber is not able to guarantee impermeability.

Hydrogen permeability means that, even at low pressure (in the range of a few mbar of positive pressure), there is a constant passage of hydrogen through said first storage membrane, resulting in the presence of hydrogen in the volume of air enclosed between the first gas storage membrane and the top pressurization membrane.

This causes obvious risks of accumulating hydrogen to the point at which the entire volume under the gasometer becomes an area at high risk of explosion (equivalent to ATEX zone 0).

Even more adversely, the presence of a constant air ventilation, which, coming from the auxiliary fan for feeding and pressurizing the gasometer, constantly flows over the surface of said first gas storage membrane, can generate the danger of locally charging this surface with electrostatic charges such as to be able to trigger even a small spark causing an explosion.

In an attempt to solve, at least partially, these problems of leak-tightness, pneumatic gasometers are known that are equipped with a third membrane placed above said first membrane and attached in an impermeable manner to at least said second membrane.

Said third membrane is adapted to delimit, coacting with said second membrane, said pressurization chamber and to define, with said first membrane, a cavity open to the outside.

Due to the presence of the third membrane, which delimits the pressurization chamber coacting with the second membrane, the degree of isolation between the two chambers is increased and the risk of gas leaks from the storage chamber entering the pressurization chamber is reduced: in fact, the third membrane forms an additional barrier to the passage of gas from one chamber to the other. Any gas losses from the storage chamber are confined to the cavity between the first membrane and the third membrane. These leaks can flow outside, as the pressure in said space, directly in contact with the atmosphere, is considerably lower than both the pressure of the gas and the pressure of the air in the pressurization chamber, but this expulsion can in fact only take place in the free space between the lower edges of the membranes, close to the ground anchoring system.

Adversely, since hydrogen has a very low molecular weight and tends to accumulate at the top of the cavity and push upwards, it is impossible for it to escape into the atmosphere through the free space between the lower edges of the membranes.

Considering that 1 m$^3$ of hydrogen weighs about 10% of an equal volume of air, it follows that each m$^3$ of hydrogen generates a vertical buoyancy of about 0.9 kg.

The hydrogen present in the cavity therefore tends to stagnate in its upper volume and is unlikely to be able to flow towards the openings along the lower edge of the membranes.

Presentation of the Invention

The purpose of the present invention is to eliminate the drawbacks and disadvantages described above.

The main object of the present invention is to produce a pneumatic membrane gasometer provided with a gas storage chamber and a pressurization chamber adjacent thereto, which significantly reduces the risk of hydrogen infiltration into the pressurization chamber, to the benefit of safety and reliability. More in detail, it is an object of the invention to ensure that any hydrogen losses due to porosity of the membranes or coming from certain points of the storage chamber flow outside instead of infiltrating into the air pressurization chamber, thereby avoiding the risk of fire or explosion of said gasometer.

The objects are achieved with a pneumatic membrane gasometer for the storage of hydrogen gas at low pressure, comprising:
 a first bag-shaped membrane, adapted to delimit a hydrogen storage chamber resting on a base surface;
 a second membrane adapted to partially delimit a pressurization chamber superimposed, at least in part, on said storage chamber;
 a third membrane, placed resting on top of said first membrane, attached in an impermeable manner at least to said second membrane, adapted to delimit, coacting with said second membrane, said pressurization chamber and to define, with said first membrane, a cavity open towards the outside of the pneumatic gasometer;
 hydrogen supply and discharge means associated with said storage chamber;
 pressurization means of said pressurization chamber by means of air, comprising fan means and valve means for regulating and discharging the air contained in said pressurization chamber;
 mechanical anchoring means of said first, second and third membranes to said base surface;
characterized in that it comprises a natural passive ventilation system, adapted to vent any hydrogen losses towards the outside, including a duct adapted to connect said cavity to the external environment through said pressurization chamber.

Advantageously, the surface of said third membrane facing said first membrane is shaped to define therewith channels for collecting and conveying any hydrogen leaks from said cavity towards said duct.

According to a first aspect of the invention, the surface of said third membrane facing said first membrane comprises spacer means from said first membrane to create said channels in said cavity.

Alternatively, these spacer means are chosen from continuous profiles, discontinuous shims or roughnesses produced on said surface.

In a preferred variant of the invention, at least said second and third membrane are made of an antistatic material.

According to a further aspect of the invention, said mechanical anchoring means comprise:
 a gasket arranged on said base surface and adapted to circumscribe said pneumatic gasometer;
 a flange placed above said gasket and also adapted to circumscribe said pneumatic gasometer;
 a plurality of bolts adapted to hold said flange in position on said gasket,
where the edges of at least said second and third membrane are superimposed on each other and clamped between said gasket and said flange.

According to a possible embodiment, said duct comprises a flexible pipe of bellows type having a first and a second end, where said first end is hydraulically connected to said third membrane by means of a first hole, and said second end is connected to the outside by means of a second hole provided on said second membrane.

Preferably, said flexible pipe of bellows type includes reinforcing rings arranged transversely thereto at folds of said bellows.

Furthermore, said duct comprises coil spring elastic means arranged between said first and said second ends of said flexible pipe.

According to further aspects of the invention:
 said second end of said flexible pipe comprises a flange;
 said second membrane comprises a protective cap for said duct placed in the vicinity of said second hole.

Even more preferably, said pneumatic gasometer comprises:
 a hydrogen detection sensor placed on the top of said pressurization chamber in the vicinity of said second hole of said second membrane;
 a plurality of lightning conductor antennas arranged around its perimeter.

In a particularly preferred variant, said first membrane comprises a base membrane and a covering membrane, attached to each other in an impermeable manner, to form said bag-shaped storage chamber.

According to a possible variant of embodiment, said pneumatic gasometer comprises a fourth membrane arranged above said base surface and below said first membrane, attached in an impermeable manner to said third membrane to produce an extension of said cavity in order to entirely circumscribe said storage chamber.

Furthermore, said pneumatic gasometer comprises a belt made of non-woven fabric interposed between said first membrane and said fourth membrane adapted to occupy said extension of said cavity.

Preferably, said fourth membrane comprises an edge arranged to be clamped between said gasket and said flange of said anchoring means coupling to the edges of at least said second and third membrane.

The main advantage obtained with the present invention derives from the presence inside the gasometer of a passive natural ventilation system by means of which the hydrogen, coming from possible leaks and losses caused by the permeability of said first membrane, is free to flow upwards inside a duct that passes through the pressurization chamber and exit into the atmosphere, thus eliminating the risk of accumulation thereof inside the volume of the gasometer.

The flexible bellows pipe with which said duct is produced creates a continuous channel of variable length and shape for the confined passage of hydrogen inside the volume comprised between said first and second membrane.

The channels for collecting and conveying any hydrogen losses present in said cavity advantageously allow the hydrogen, which permeates through the storage membrane, to flow upwards, also due to its very low specific weight.

The spacer means present on the surface of the third membrane facing the cavity create drainage and conveying channels that have a much lower resistance to flow with respect to the resistance of the third membrane with low permeability.

The antistatic material of which the membranes are made is able to limit the production and local accumulation of electrostatic charges that can generate dangerous electrical discharges potentially triggering an explosion if in an atmosphere with a hydrogen concentration of more than 4%.

The reinforcing rings placed transversely to said flexible pipe give it stability and withstand the forces generated by the pressure of the compressed air inside the pressurization chamber.

Said elastic means provided along said flexible pipe allow it to remain in a prevalently vertical position during all loading and unloading steps of the chamber delimited by the first storage membrane, so as to optimize the natural outflow of hydrogen.

Even more advantageously, the tensile force generated by the elastic means creates an upward vertical pull on the third membrane in the vicinity of the fixing point of the flexible pipe, with the consequent effect of creating a cusp that facilitates the natural upward collection of the hydrogen flow.

BRIEF DESCRIPTION OF THE DRAWINGS

These and other advantages will be clearer and more evident from the description of the invention, set down below with the aid of the drawings representing some examples of embodiment, illustrated by way of non-limiting example, wherein.

DETAILED DESCRIPTION OF PREFERRED EMBODIMENTS OF THE INVENTION

Figure 1:
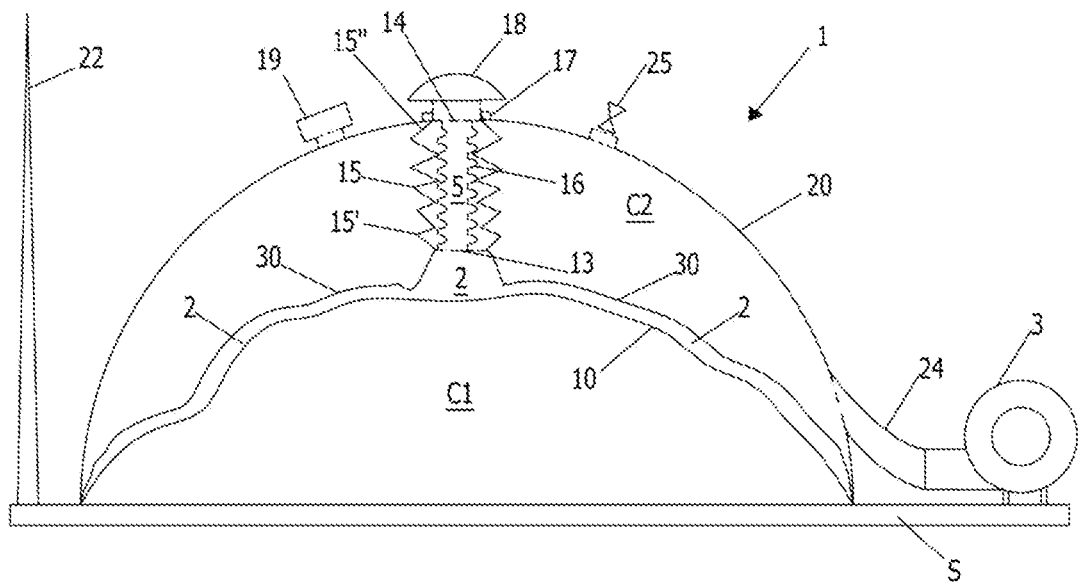
FIG. 1 illustrates, in cross-section along a vertical plane, a pneumatic membrane gasometer according to the invention.

FIG. 1 illustrates a pneumatic membrane gasometer 1 for the storage of hydrogen at low pressure.

The entire pneumatic gasometer 1 rests on a base surface S, advantageously formed by an impermeable concrete base, and is anchored thereto.

The pneumatic gasometer 1 of the present invention comprises a first membrane 10 and a second membrane 20. Said first membrane 10 delimits a hydrogen gas storage chamber C1, while said second membrane 20 partially delimits an air pressurization chamber C2.

Said first membrane 10 can be made in one piece, closed on itself and bag-shaped, or can comprise, as in the variant illustrated, a base membrane 10a and a covering membrane 10b, fixed to each other in an impermeable manner by welding along their respective edges to form said storage chamber C1.

Gas supply and discharge means (not illustrated) are connected to said storage chamber C1, while pressurization means are connected to said pressurization chamber C2.

Said gas supply and discharge means comprise suitable pipes and flanged connections on the first storage membrane 10, while said pressurization means advantageously comprise a fan 3 (or air compressor) and pipes 24 connected to the second membrane 20.

Said pneumatic gasometer 1 comprises a third membrane 30, placed resting on top of said first membrane 10, fixed in an impermeable manner at least to said second membrane 20, adapted to delimit, coacting with said second membrane 20, said pressurization chamber C2 and to define, with said first membrane 10, a cavity 2 open towards the outside of the pneumatic gasometer 1.

For this purpose, said pneumatic gasometer 1 comprises a passive natural ventilation system, adapted to vent any hydrogen losses towards the outside, comprising a duct 5 adapted to connect said cavity 2 to the outside environment passing through said pressurization chamber C2.

Figure 2:
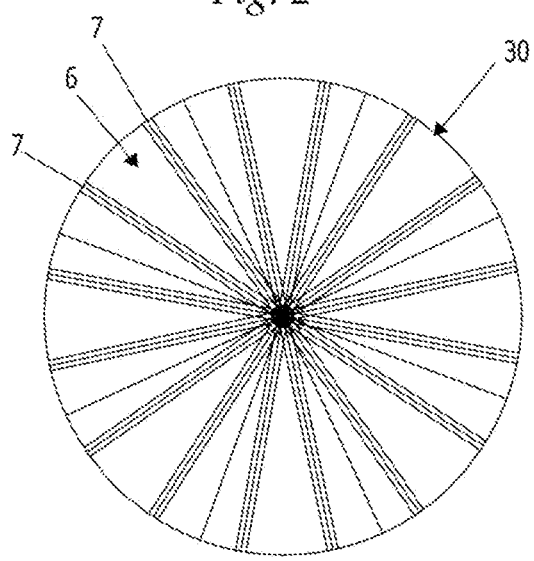
FIG. 2 illustrates, in a flat bottom view, a component of the pneumatic gasometer of FIG. 1.

With particular reference to FIG. 2, the lower surface of said third membrane 30, i.e. facing said first membrane 10, is shaped to define therewith channels 6 for collecting and conveying any hydrogen losses permeated by said first membrane 10 and collected in said cavity 2.

Said channels 6 have the task of conveying the hydrogen towards the top of said cavity 2 and then towards said duct 5.

In order to create said channels 6 in said cavity 2, the surface of said third membrane 30 facing said first membrane 10 comprises spacer means 7 from said first membrane 10, i.e. protruding elements, of continuous or discontinuous type, obtained from said membrane or applied thereto.

Said spacer means 7 are chosen from continuous profiles arranged radially below said surface or discontinuous shims placed uniformly below said surface.

Figure 3A:
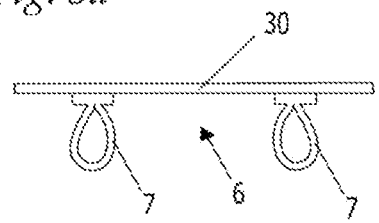
FIGS. 3a, 3b, 3c illustrate, in section, a detail of FIG. 2 according to different possible variants of embodiment.
Figure 3B:
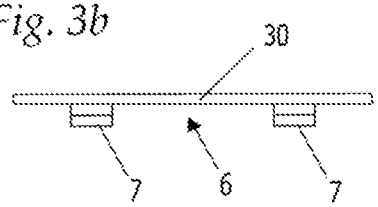
Figure 3C:
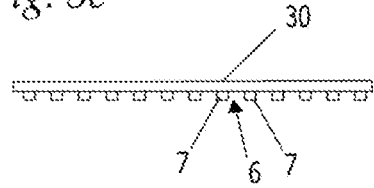

FIGS. 3a, 3b and 3c illustrate different types of spacer means 7, protruding to a greater or lesser extent and spaced apart by a greater or lesser distance.

In order to create said channels 6 in said cavity 2, the roughness of the surface of said third membrane 30 might even be sufficient; in the case of direct contact between the two membranes 10, 30, the roughness of the lower surface of said third membrane 30 creates empty micro-channels into which hydrogen can infiltrate to flow upwards.

For this purpose, while said first membrane 10 is made of fabric coated with PVC on both faces, said third membrane 30 is also made of fabric, but with the face in contact with the first membrane 10 coated with a material other than PVC, for example with lubricating properties, advantageously silicone, so as to prevent the membranes from adhering to each other and thus leave the collection space for permeated hydrogen.

Said duct 5 comprises a flexible pipe 15 of bellows type having a first end 15' and a second end 15", where said first end 15' is hydraulically connected to said third membrane 30 by means of a first hole 13, and said second end 15" is connected to the outside by means of a second hole 14 provided on said second membrane 20.

Said holes 13, 14 are both provided on the tops of the respective membranes 30, 20.

Said second end 15" of said flexible pipe 15 comprises a flange 17 for fixing to the second membrane 20.

In order to prevent the entry of rain or other objects from outside, said second membrane 20 comprises a protective cap 18 for said duct 5 at said second hole 14.

Said flexible pipe 15 creates a confined continuous channel, connecting said cavity 2 to the external environment, which passes through the pressurization chamber C2 for the passage of hydrogen.

By producing said flexible pipe 15 with deformable bellows, for example made of rubber, it is possible to offset any mutual movements between the membranes 30, 20.

To allow the flexible pipe 15 to maintain a continuous channel in a prevalently vertical position so as to optimize the natural flow of hydrogen exiting into the atmosphere, elastic means 16 are inserted into said pipe, which in fact keep it tensioned in relation to the third membrane 30.

Said elastic means 16, of coil spring type, are arranged between said first 15' and said second 15" end of said flexible pipe 15.

Moreover, said flexible pipe 15 of bellows type comprises reinforcing rings (not illustrated), arranged transversely thereto preferably in the folds of said bellows.

In order to improve its functionality, said pneumatic gasometer 1 comprises various safety measures and devices.

To reduce the risk of electrically charging the second membrane 20, in the vicinity of the flange 17 for fixing the flexible pipe 15, this is made of an antistatic material. Similarly, said third membrane 30 also comprises an antistatic material.

Said gasometer 1 comprises a valve 25 for regulating and discharging pressurization air, placed on the top of said second membrane 20 so as to flush the air present in the pressurization chamber C2, diluting and eliminating into the atmosphere any possible hydrogen leaks caused by cuts or damage to the third membrane 30.

Moreover, said gasometer comprises a system of perimeter lightning protection antennas 22 that further eliminates the risk of ignition from atmospheric discharges.

Finally, said gasometer 1 comprises a hydrogen leak sensor 19 placed near the top of the second external membrane 20: in case of serious damage, it is able to notify the user of the presence of an explosive mixture of hydrogen in air, with the consequent emission of an alarm that allows the operator of the plant to immediately shut off the flow of hydrogen to the gasometer and to empty the remaining content by means of vent valves (not illustrated) specifically provided on the gas line.

Figure 5:
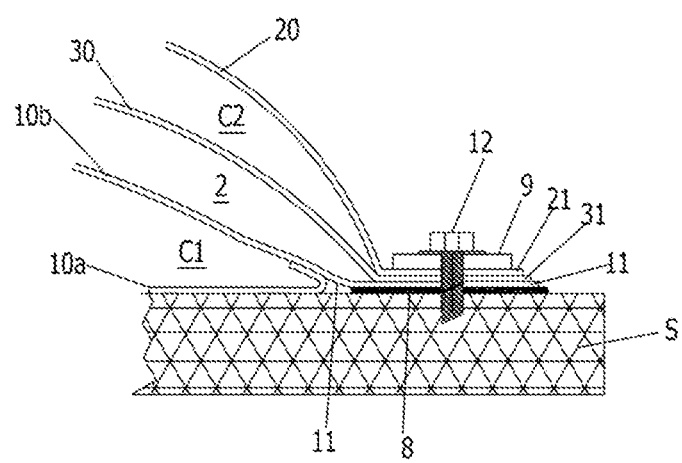
FIG. 5 illustrates, in cross-section, a detail of the ground anchoring of the pneumatic gasometer of FIG. 1.
Figure 6:
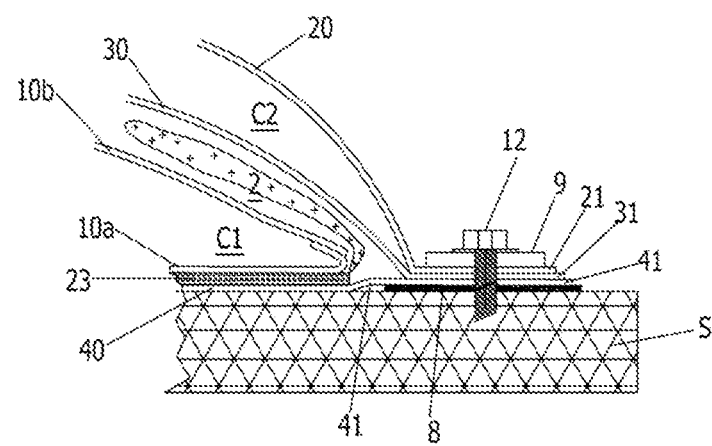
FIG. 6 illustrates, in cross-section, a particular variant of embodiment of the pneumatic gasometer according to the invention also with reference to its ground anchoring system.

With particular reference to FIGS. 5 and 6, the mechanical anchoring means 4 of said membranes 10, 20, 30 to said base surface S of the pneumatic gasometer 1 are illustrated.

As for operation of the pneumatic gasometer 1 it is important for all three membranes 10, 20, 30 to be fixed to each other in an impermeable manner, said mechanical anchoring means 4 are also of gas-tight type.

The covering membrane 10b of said first membrane 10, once welded to the corresponding bottom membrane 10a, also extends to produce a free edge 11.

In the variant of FIG. 5, said mechanical anchoring means 4 comprise:
  a gasket 8 arranged on said base surface S and adapted to circumscribe said pneumatic gasometer 1;
  a flange 9 placed above said gasket 8 and also adapted to circumscribe said pneumatic gasometer 1;
  a plurality of anchor bolts 12, or steel tie rods, adapted to hold said flange 9 in place on said gasket 8,
where the edges 11, 21, 31 of said membranes 10, 20, 30 are superimposed on each other and clamped between said gasket 8 and said flange 9.

Said anchor bolts 12 ensure a mechanical spot fixing of the flange 9 to the base surface S, while said gasket 8 ensures uniform contact with the base surface S.

With particular reference to FIG. 6, said pneumatic gasometer 1 comprises a fourth membrane 40 arranged above said base surface S and below said bottom membrane 10a of said first membrane 10.

Said fourth membrane 40 is impermeably fixed to said third membrane 30 to produce an extension of said cavity 2, so that said cavity 2 entirely circumscribes said storage chamber C1.

Said cavity 2 thus also collects any hydrogen losses directed towards said base surface S, below the gasometer 1, and conveys them towards said natural passive ventilation system 5.

Said fourth membrane 40 has the same characteristics as said third membrane 30, and is therefore made of antistatic fabric coated with PVC and only siliconized on the side facing the bottom membrane 10a.

Said gasometer 1 comprises a belt 23 made of TNT interposed between the bottom membrane 10a of said first membrane 10 and said fourth membrane 40, adapted to occupy said extension of said cavity 2 and to act as spacer between the two membranes 10, 40 and as distributor of hydrogen losses.

As, due to the weight of said gasometer, it would be difficult for channels to collect and convey hydrogen to resist in the extension portion of the cavity 2, this was overcome by using the micro-channels present in the TNT belt 23.

To ensure continuity of said cavity 2, all around said storage chamber C1, said third 30 and fourth 40 membranes must also be sealed to each other in a gas-tight manner.

Making use of the mechanical anchoring means 4 described above, the free edge 41 of said fourth membrane 40 is also arranged between said gasket 8 and said flange 9, placed underneath the previously coupled edges 21, 31 of the two membranes 20, 30 already impermeably fixed to each other.

In this case, said first bag-shaped membrane 10 comprises discontinuous anchors (not illustrated), in the shape of a band and arranged radially, which are clamped in turn in the anchoring means 4 between gasket 8 and flange 9 with the sole function of holding said bag of the storage chamber C1 in position.

Alternatively, if the first membrane 10 were to comprise the free edge 11, this latter would be provided with openings placed in the vicinity of the chamber C1, adapted to connect the lower part of the cavity to the upper part, to help the hydrogen to rise towards the duct 5.

Figure 4:
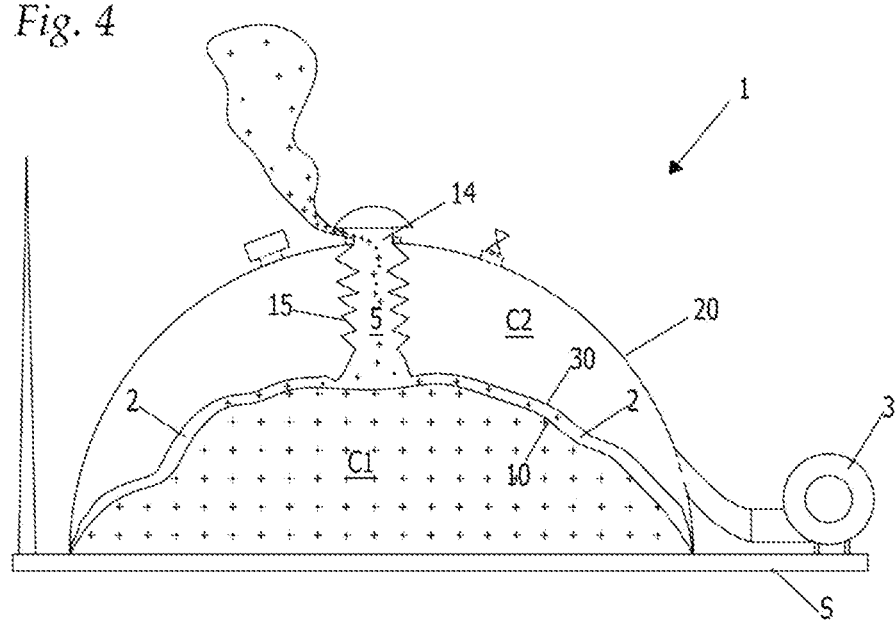
FIG. 4 illustrates, in cross-section along a vertical plane, a pneumatic membrane gasometer according to the invention, partially filled with hydrogen and in operation.

With particular reference to FIGS. 4 and 6, operation of the pneumatic membrane gasometer 1 according to the invention is illustrated.

During operation of the pneumatic gasometer 1, the storage chamber C1 fills with or empties itself of hydrogen, changing its shape and volume, while the pressurization chamber C2, which follows it in the change of volume, is maintained at a certain pressure level by the said pressurization means.

The thrust exerted by the chamber C2 on the adjacent chamber C1 allows gas to be delivered at the desired pressure and facilitates emptying of the storage chamber C1.

Any hydrogen that escapes from the storage chamber C1 into the space between the first membrane 10 and the third membrane 30 and, if applicable, the fourth membrane 40, are collected in the cavity 2 created thereby and are released directly into the atmosphere through said passive natural ventilation system, i.e. said duct 5, preventing hydrogen infiltration into the pressurization chamber C2 and the consequent risk of fire or explosion.

In particular, any hydrogen losses are released to the outside through said flexible bellows pipe 15 that connects the top of the third membrane 30, where the hydrogen that pushes upwards in fact tends to accumulate, to the outside environment above the pressurization chamber C2.

The invention claimed is:

1. Pneumatic membrane gasometer for the storage of hydrogen gas at low pressure, comprising:
   a first bag-shaped membrane adapted to delimit a hydrogen storage chamber resting on a base surface;
   a second membrane adapted to partially delimit a pressurization chamber superimposed, at least in part, on said storage chamber;
   a third membrane, placed resting on top of said first membrane, fixed in an impermeable manner at least to said second membrane, adapted to delimit, coacting with said second membrane, said pressurization chamber and to define, with said first membrane, a cavity open towards the outside of said pneumatic gasometer;
   hydrogen supply and discharge means associated with said storage chamber;
   pressurization means of said pressurization chamber by mean of air, comprising fan means and valve means for regulating and exhausting the air contained in said pressurization chamber;
   mechanical anchoring means to said base surface of said first, second and third membranes;
the pneumatic membrane gasometer further comprising a natural passive ventilation system, adapted to vent any hydrogen leaks towards the outside, comprising a duct adapted to connect said cavity to the outside environment passing through said pressurization chamber.

2. The pneumatic membrane gasometer according to claim 1, wherein the surface of said third membrane facing said first membrane is shaped to define therewith channels for collecting and conveying any hydrogen losses from said cavity towards said duct.

3. The pneumatic membrane gasometer according to claim 2, wherein the surface of said third membrane facing said first membrane comprises spacer means from said first membrane to create said channels in said cavity.

4. The pneumatic membrane gasometer according to claim 3, wherein said spacer means are chosen from continuous profiles, discontinuous shims or roughnesses produced on said surface.

5. The pneumatic membrane gasometer according to claim 1, wherein at least said second and third membranes are made of an antistatic material.

6. The pneumatic membrane gasometer according to claim 1, wherein said mechanical anchoring means comprise:
   a gasket arranged on said base surface and adapted to circumscribe said pneumatic gasometer;
   a flange placed above said gasket, and also adapted to circumscribe said pneumatic gasometer;
   a plurality of anchor bolts adapted to hold said flange in position on said gasket,
where edges of at least said second and third membranes are superimposed on each other and clamped between said gasket and said flange.

7. The pneumatic membrane gasometer according to claim 1, wherein said duct comprises a flexible pipe of bellows type having a first and a second end, where said first end is hydraulically connected to said third membrane by means of a first hole, and said second end is connected to the outside through a second hole provided on said second membrane.

8. The pneumatic membrane gasometer according to claim 7, wherein said flexible pipe of bellows type comprises reinforcing rings arranged transversely thereto at folds in said bellows.

9. The pneumatic membrane gasometer according to claim 7, wherein said duct comprises coil spring elastic means arranged between said first and said second ends of said flexible pipe.

10. The pneumatic membrane gasometer according to claim 7, wherein said second membrane comprises a protective cap for said duct placed at said second hole.

11. The pneumatic membrane gasometer according to claim 7, further comprising a hydrogen detection sensor placed on the top of said pressurization chamber in the vicinity of said second hole of said second membrane.

12. The pneumatic membrane gasometer according to claim 1, wherein said first membrane comprises a bottom membrane and a covering membrane, fixed to each other in an impermeable manner, to form said storage chamber.

13. The pneumatic membrane gasometer according to claim 1, further comprising a fourth membrane arranged above said base surface and below said first membrane, impermeably fixed to said third membrane to produce an extension of said cavity in order to entirely circumscribe said storage chamber.

14. The pneumatic membrane gasometer according to claim 13, further comprising a belt made of TNT interposed between said first membrane and said fourth membrane adapted to occupy said extension of said cavity.

15. The pneumatic membrane gasometer according to claim 6, further comprising a fourth membrane arranged above said base surface and below said first membrane, impermeably fixed to said third membrane to produce an extension of said cavity in order to entirely circumscribe said storage chamber,
   wherein said fourth membrane comprises an edge arranged to be clamped between said gasket and said flange of said anchoring means coupling to the edges of at least said second and third membranes.

* * * * *